United States Patent
Hoppe (10) Patent No.: US 8,386,025 B2
(45) Date of Patent: Feb. 26, 2013

(54) DEVICE AND METHOD FOR MONITORING MUSCULAR ACTIVITY

(75) Inventor: Karsten Hoppe, Copenhagen (DK)

(73) Assignee: IctalCare A/S, Delta, Horsholm (DK)

( * ) Notice: Subject to any disclaimer, the term of this patent is extended or adjusted under 35 U.S.C. 154(b) by 169 days.

(21) Appl. No.: 12/597,994

(22) PCT Filed: Apr. 28, 2008

(86) PCT No.: PCT/DK2008/050097
§ 371 (c)(1),
(2), (4) Date: Dec. 1, 2009

(87) PCT Pub. No.: WO2008/131782
PCT Pub. Date: Nov. 6, 2008

(65) Prior Publication Data
US 2010/0137735 A1    Jun. 3, 2010

(30) Foreign Application Priority Data
Apr. 30, 2007 (DK) ................................. 2007 00640

(51) Int. Cl.
*A61B 5/00* (2006.01)
(52) U.S. Cl. ..................................................... 600/546
(58) Field of Classification Search .................. 600/546, 600/587, 595
See application file for complete search history.

(56) References Cited

U.S. PATENT DOCUMENTS

| | | | |
|---|---|---|---|
| 5,263,489 A | 11/1993 | Johnson | |
| 6,238,338 B1 | 5/2001 | Deluca et al. | |
| 6,440,067 B1 * | 8/2002 | DeLuca et al. | 600/300 |
| 2002/0177882 A1 | 11/2002 | Dilirenzo | |
| 2003/0109905 A1 * | 6/2003 | Mok et al. | 607/60 |
| 2005/0277844 A1 * | 12/2005 | Strother et al. | 600/546 |
| 2006/0004299 A1 * | 1/2006 | Endo et al. | 600/546 |

FOREIGN PATENT DOCUMENTS

| | | |
|---|---|---|
| WO | WO2004/066832 A | 8/2004 |
| WO | WO2006/008334 A | 1/2006 |
| WO | WO2006/094513 A | 9/2006 |
| WO | WO 2006094513 A2 * | 9/2006 |
| WO | WO2007/034476 A | 3/2007 |

OTHER PUBLICATIONS

International Search Report.

* cited by examiner

*Primary Examiner* — Max Hindenburg
(74) *Attorney, Agent, or Firm* — William J. Sapone (57) ABSTRACT

An apparatus and a method for monitoring muscle activity are provided. The apparatus comprises a sensor for detecting the generated electromyographic signals and processing means. The processing means generates an event signal if the electromyographic signal exceeds a predetermined power content within a predetermined time window. The event signal triggers an event, which may be an alarm. The apparatus further comprises communication means for transmitting the detected electromyographic signals from the sensor to the processing means. The means comprises the steps of detecting and evaluating the electromyographic signals. Furthermore, the method comprises generating an event signal and triggering an event by the event signal.

32 Claims, 7 Drawing Sheets

DEVICE AND METHOD FOR MONITORING MUSCULAR ACTIVITY

FIELD OF THE INVENTION

The present invention relates to an apparatus and a method for monitoring muscle activity.

BACKGROUND

Health providers today need condensed and specific information from their patients in order to provide an improved treatment. In particular within areas where the muscle activity can shed a light on the status of the patient continuously monitoring is desirable. Such areas may for example be epilepsy, where patients can experience motor convulsions caused by excessive muscle activity. Furthermore, with increased focus on financial management of health care there is a need for monitoring patients at home and in heir everyday environment in order to effectively and properly diagnose and treat a patient.

Today patients or their caregivers observe and register seizures primarily by using a sheet whereon they have to fill in when they have had an epileptic seizure and preferably the duration. However, this can be very complicated as some times the patient will never notice a seizure as some seizures may be very subtle or in other situations the patient becomes unconscious and may wake up without knowing a seizure has occurred or do not know the duration or type of seizure. Thus, the data collected by the patients own input are usually very unreliable.

Moreover, apparatus and methods for monitoring patients and/or users in their daily environment need not only be reliable but also discreet and comfortable.

WO 95/15117 discloses monitoring of a motor activity signal which is separate from the monitoring of the brain activity signal. When the motor activity signal amplitude is within a predetermined motor window, a motor activity counter is incremented. When the motor activity signal amplitude is outside the predetermined motor window, the motor activity counter is decremented. An epileptic seizure is indicated when the motor activity counter value lies above a motor threshold.

However, many types of epileptic seizures exists and not all generate a heavy muscle activity but may instead generate subtle spasm where many different requirements has to be checked in order to determine that it is indeed an epileptic seizure. Thus, sophisticated monitoring devices are needed which beside occurrence of the motor convulsion also is capable of monitoring e.g. extent and/or the amplitude of the convulsion or other pan-peters which are relevant to epileptic seizures.

U.S. Pat. No. 6,440,067 discloses a method and system for remotely monitoring and identifying so-called Functional Activities by identifying specific signal patterns which correspond to a given Functional Activity.

In order to identify a signal pattern, in particular patterns from electromyographic signals, a high sampling rate as well as a significant time span is necessary. This requires a high level of processing which consequently requires a lot of power consumption. Thus, for use in devices where a low power consumption is preferred, i.e. due to size and/or battery lifetime, such a method would be inappropriate.

Moreover, while using a method for comparing signal patterns may be suitable in order to recognize controllable and repeatable activities such as walking, lifting etc., it is not suitable to use in order to detect epileptic seizures. An epileptic seizure is an uncontrollable action caused by abnormal electrical activity in the brain which generates signals that are individually different.

SUMMARY

In one aspect the present invention relates to an apparatus for detecting electromyographic signals and monitoring muscle activity, said apparatus comprises, —a sensor, for detecting the electromyographic signals; processing means, wherein an event signal is generated if the electromyographic signals is above a predetermined power content within at least one predetermined time window and wherein the event signal triggers an event; and first communication means, for transmitting the detected electromyographic signals from the sensor to the processing means.

The term 'electromyographic signal' should be understood as the representation of the continuous measuring of skeletal muscle activity generated by the electrical activity of the muscle fiber/fibers during contraction Seeing as the 'electromyographic signal' thus is a theoretic representation of the electrical activity during muscle activity the 'detected electromyographic signal' is the signal or signals, which are detected by a sensor or other electronics and are a measurable signal which may be processed and analyzed by either digital or analogue means. Such 'detected electromyographic signals' are often subject to interference, quality of the electronic components and other so-called noise. Thus the 'detected electromyographic signals' often contain information of the muscle activity while at the same time contains a lot of undesirable noise, while the 'electromyographic signal' is the clean representation of the muscle activity.

By evaluating the detected electromyographic signal within a predetermined time window it is possible to obtain an immediate indication of the muscle activity without influence from earlier measurements. Such earlier measurements may otherwise cause the result to deviate undesirably.

Furthermore, by having a set number of predetermined requirements it is possible to distinguish between different activities as some muscle activities will fulfill one set of requirements while other muscle activities will fulfill another set of requirements. Typically the set of predetermined requirements are in the form of a number of parameters, which when fulfilled within the time window triggers an event signal, e.g. in the form of an alarm signal which activates an alarm.

For example when measuring epileptic seizures different predetermined sets of requirements may help detect different types of seizures, e.g. they may help distinguish between myoclonic seizures, clonic seizure and/or tonic-clonic seizures.

It should be understood that an event signal may be in many different forms and trigger many different kinds of events. In one example the event signal may be a simple on/off indication, for example by a simple digital binary signal, which is transmitted every second. If the electromyographic signals are not above a predetermined power content the event signal transmits an 'off' for example in the shape of a binary zero, however, if then, electromyographic signal are above a predetermined power content the event signal transmits an 'on' for example in the shape of a binary one and an event is activated, for example an alarm.

Other events may simply be recording of data on storage device or specific colouring or other marking of a part of a plotted signal representing the electromyographic signals.

In one embodiment the processing means is comprised within the sensor. This allows for an all in one component which can process the data and e.g. save it for later retrieval in case a storage element is provided together with the processing means. Alternatively the processed data and/or the event signal can be transmitted to a peripheral device.

The term 'data' should be understood broadly as this includes the sum of information which are being analyzed, transmitted or otherwise processed by the apparatus according to the invention. Thus it may include the detected electromyographic signal and an event signal if both are stored on a storage device or transmitted to e.g. another computer unit.

In another embodiment the processing means is comprised within a peripheral device. Such peripheral devices can be different handheld units, such as a PDA (Personal Digital Assistant), an iPOD® or a cell phone. It can also be a personal computer, i.e. a laptop, a desktop computer or a custom made unit manufactured for the specific application of analyzing and monitoring the muscle activity.

This allows for external monitoring of the muscle activity by the user him/herself, a nurse or other caregivers. In one example the peripheral device collect data and monitors muscle activity during the day. Later the data may be transferred to a personal computer for more thorough analyzing. The data may alternatively be transmitted directly to a personal computer, for example through the Internet. The personal computer may be placed geographically in a completely different place. The person skilled in the art can provide many different combinations of such peripheral devices and their set-ups.

Where the sensor and the processing means are physically separated many different means for transmission between the two may be provided. Thus, in one embodiment the first communication means is wireless transmission. Such wireless transmission can for example be WLAN, Bluetooth, Zigbee or infrared or any other standardized and known communication means.

It should be understood that the event triggered may serve many different purposes. In one embodiment an alarm is activated if the event is triggered. This is to alert a person, such as the user or the caring personnel that something out of the ordinary is occurring. Such an alarm can be visual, e.g. a light blinking; audio, e.g. a beeping sound; and/or tangible, e.g. a vibrating movement. The alarm can occur from the sensor, the peripheral device or a third device that communicates with the sensor.

In other embodiment the triggered event may be that a software on a personal computer register muscle activities and store them for later analysis or for a user to view the muscle activity throughout a period of time, for example through the day.

It can be understood from the above that the present apparatus can further allow monitoring during normal every day living activities with discreteness, since the portable part of the device, i.e. the sensor unit or units can be worn on one or more of the large muscles such as; Vastus Lateralis, Rectus Femoris, Biceps Brachii or Erector Spinae. The handheld unit can easily be carried by the user, for example in a pocket or in a belt.

In one embodiment the apparatus may comprise two or more sensors for detecting the electromyographic signals.

Providing multiple sensors provides a more reliable detection of muscle activity as several sensors can be placed on the skin surface on one muscle, a muscle group or other muscles where it is of interest to monitor muscle activity.

By providing several sensors on one muscle or muscle group a higher reliability is obtained as detected electromyographic signals may be compared and an average determined. Furthermore, in case one sensor is defect or is not applied correctly significantly different signals will be detected indicating that one of the sensors is not operating correct.

Furthermore, the sensors may be placed on different muscles in order to more reliably detect an epileptic seizure. Thus, if the sensors are placed on different muscles which usually contract during seizure it is possible to sort out situations where one muscle would exhibit activity indicating a seizure while the other muscle exhibit activity that indicates that no seizure is occurring. This could for example be under heavy work where specific muscles might generate electromyographic signals which are above a predetermined power content.

Yet in another embodiment two sensors can be placed on respective muscles in antagonistic pairs of muscles, such as the biceps and triceps. During regular activities such antagonistic pairs will not contract at the same time. However during epileptic seizures, in particular generalized seizures, all muscles will contract also the antagonistic pair. Thus, registering a contraction on sensors placed on the antagonistic pair may be used as an indication of an epileptic seizure.

In such apparatus with several sensors many different embodiments can be provided. Each sensor can for example be provided with processing mean and/or communicate with each' other and transmit a common event signal or alarm signal to a peripheral device. In other embodiment the sensor simply transmit the detected electromyographic signals to a peripheral device.

In another aspect the invention relates to a method for monitoring muscle activity based on an electromyographic signal, comprising the steps of: detecting the electromyographic signal; evaluate whether the electromyographic signal is above a predetermined power content within a first predetermined time window of the electromyographic signal; generate an event signal if the electromyographic signal is above the predetermined power content; and trigger an event if an event signal is generated.

This provides a method where no history of previous recorded data influences the result. This, a precise momentary indication of muscle activity may be provided.

Furthermore, by looking at the power content of the signal it is not necessary to reconstruct the entire electromyographic signal, whereby a method having a lower power consumption may be provided.

The term 'power content' encompasses the work performed by a muscle over a period of time. This may be represented and derived from the electromyographic signal in many different ways, for example by looking at the amplitude at the signal at a specific time; looking at the energy content over a period of time (e.g. by integration as described herein); or looking at the energy content within a frequency band at a specific point in time (e.g. by frequency transformation as described herein). Accordingly it may be understood that the power content is a numerical value representing said power content. Such numerical value is easily and quickly comparable with a threshold value.

An electromyographic signal will fluctuate considerably, especially when considerable muscle activity is occurring. Thus, if looking at the electromyographic signal at a random point in time chances are relative large that this point will show little or no signal indicating little or no muscle activity even if the opposite is the case.

Thus, in one embodiment the electromyographic signal is transformed into a representative signal better indicating whether muscle activity is present.

In one such embodiment an integration algorithm is applied to the electromyographic signal and the event signal is generated if the set of requirements are fulfilled for the resulting integrated electromyographic signal. This will for example indicate the power output the muscles have performed over time. By setting a threshold value at a certain amount of power within a time window as the set of predetermined requirement, an event can be triggered if the threshold value is exceeded.

Integration of the electromyographic signal may be performed analogue or digitally. Both these methods for integrating an analogue signal in general are known to the person skilled in the art.

In another embodiment the set of requirements are fulfilled if the integrated electromyographical signal within the first predetermined window has an integrated value above a predetermined threshold value for a predetermined number of times within a second predetermined sub-time window. Such predetermined number of times can be four and the second predetermined sub-time window can be five seconds. This can be applied when it is desirable to be alerted when muscle activity corresponding an epileptic seizure is occurring.

In another embodiment where it is desirable to be alerted when the muscle activity corresponds to an epileptic seizure the predetermined threshold value can be greater than the maximum voluntary contraction value of the user. Alternatively or additionally the integration algorithm is a RMS (Root Mean Squared) evaluation of the electromyographic signal.

When first presented with the problem the person skilled in the art will understand how to apply an RMS algorithm to a detected electromyographic signal. Furthermore, a person skilled in the art would also be able to apply other averaging or smoothing algorithms such as moving average and envelope functions.

As described above, the event triggered may be an alarm to thereby alert the user or caregivers of an epileptic seizure.

In another embodiment wherein the electromyographic signal is transformed into a representative signal a frequency transformation algorithm is applied to the electromyographic signal and the event signal is generated if the set of requirements are fulfilled for the resulting frequency transformed electromyographic signal.

The frequency profile of the electromyographic signal will change over time and during strenuous muscle activity as e.g. due to muscle fibre fatigues or pathological effects.

Thus, monitoring within the frequency domain may for example be of interest within muscle training as it will be possible to focus the work and to monitor when relevant muscle fatigue occurs.

In one embodiment the transformation algorithm is a fourier transformation of the electromyographic signal. Such fourier transformation may for example be performed on the electromyographic digitally after the electromyographic signal has been converted from an analogue signal to a digital signal, as would be understood by the person skilled in the art.

FIGURES

FIG. 1a shows schematically an apparatus according to the invention, FIG. 1b showing an enlarged view of a sensor including a sensor processing unit, FIG. 5c shows an enlarged section of FIG. 5a.

DETAILED DISCLOSURE

Figures 1A, 1B:
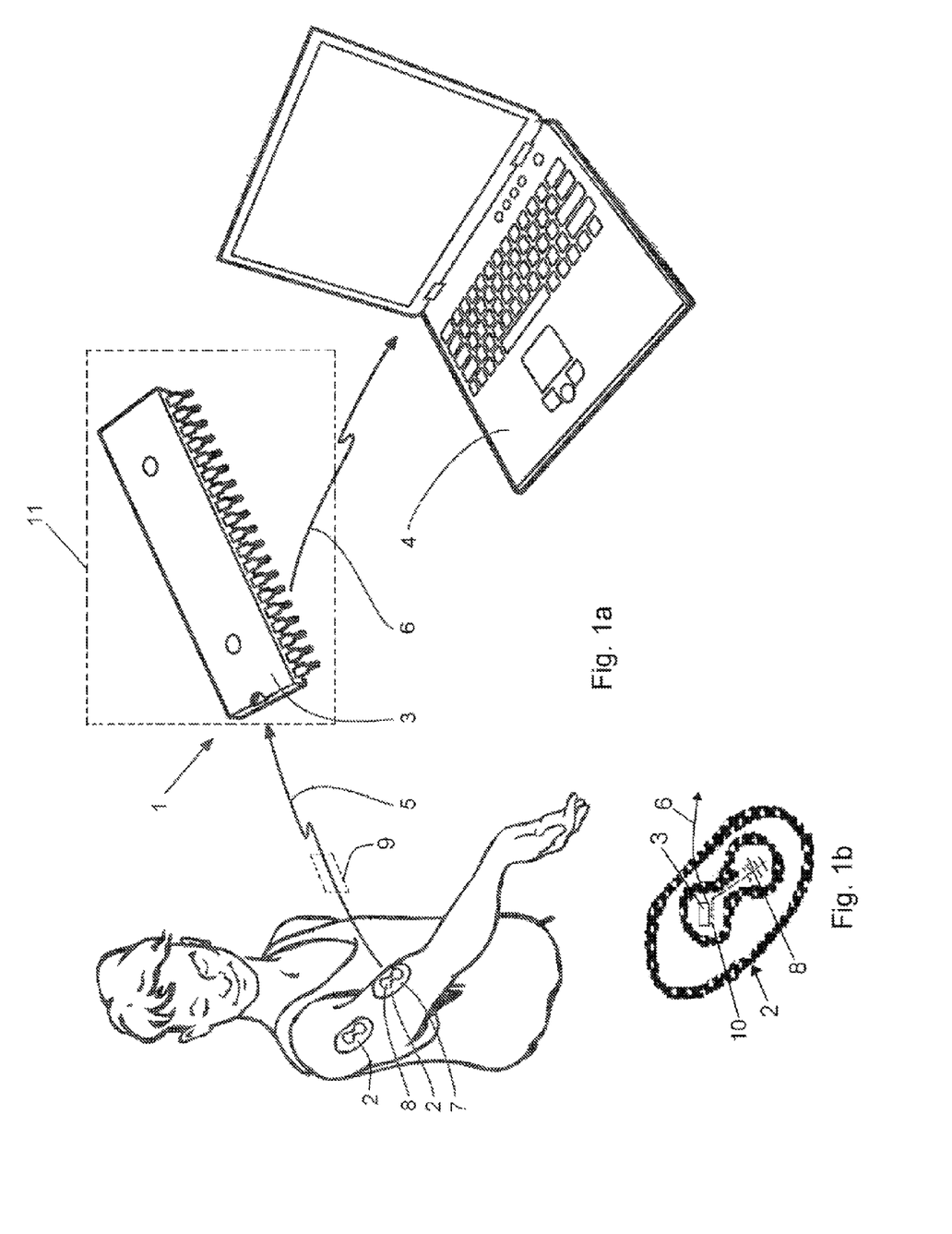

FIG. 1a shows a basic schematic of a monitoring system 1 according to the invention. The monitoring system is basically made up of three components; a sensor unit 2, a signal processing unit 3 and an alarm unit 4. As shown, two or more sensor units 2 may be used.

The sensor unit 2 detects electromyographic signals from a wearer. The sensor unit comprises an adhesive patch 7 which is adhered to the skin of a user. A sensor circuitry 8 for detecting the electromyographic signals can be arranged within, on top or on the bottom of the patch. Such patches are for example known from published international patent application WO 2006/094514.

The sensor circuitry transmits the detected electromyographic signals to the signal processing unit 3 through first communication means 5.

The signal processing means 3 contains a program which compares the electromyographic signals against a predetermined set of requirements. If the electromyographic signals fulfils these requirements the signal processing means 3 generates an alarm signal which is emitted to the alarm unit 4 through second communication means 6. As illustrated in FIG. 1a, a frequency filter 9 may optionally be used for frequency filtering the electromyographic signal before the electromyographic signal is evaluated. The frequency filter may be a bandpass filter, lowpass filter or a highpass filter.

Within the scope of the present invention it should be understood that the basic schematic shown in FIG. 1a may be implemented for use in many different ways. As mentioned the sensor unit 2 may for example be provided as a patch wherein a sensor circuitry is provided. As shown in FIG. 1b, the signal processor unit 3 may also be included in said sensor circuitry whereby the first communication means simply is an electric connection 10 between the sensor circuitry 8 and the signal processor unit 3.

Alternatively the signal processor 3 may be provided in a separate physical unit, i.e. a peripheral device 11, as illustrated in broken lines in FIG. 1a. This can for example be a handheld appliance such as a PDA (Personal Digital Assistant), a cellular phone, an iPOD® or a self contained unit. Thus the first communication means may advantageously be a wireless connection between the sensor unit and the separate physical unit. Such wireless connection may for example be provided through Bluetooth, WLAN, Zigbee or other known wireless protocols and transmitting means.

In basically the same way as described above the second communication means 6 may also be wireless, whereby the alarm signal may be sent to a separate alarm unit such as a buzzer or a light.

Alternatively the alarm unit may be a personal computer, which both can collect and store received alarm signals and sound an alarm when an alarm signal is received.

In yet another embodiment the signal processing unit 3 and the alarm unit 4 may be provided in the same unit, for example in a handheld appliance as described above or a personal computer or other peripheral device. Alternatively they may be provided in a wrist watch whereby a user may be able to monitor his/hers muscle movement at any time FIG. 2a shows an electromyographic signal plotted with the potential of the signal [mV] as a function of time [sec].

Figure 2A:
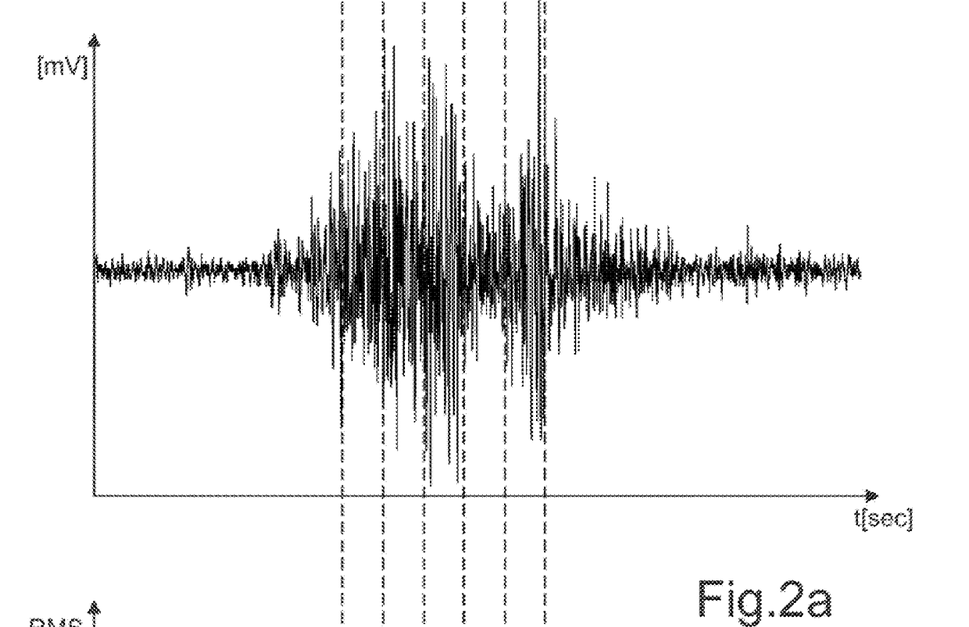
FIGS. 2a and 2b shows the evaluation of an electromyographic signal according to the invention.
Figure 2B:
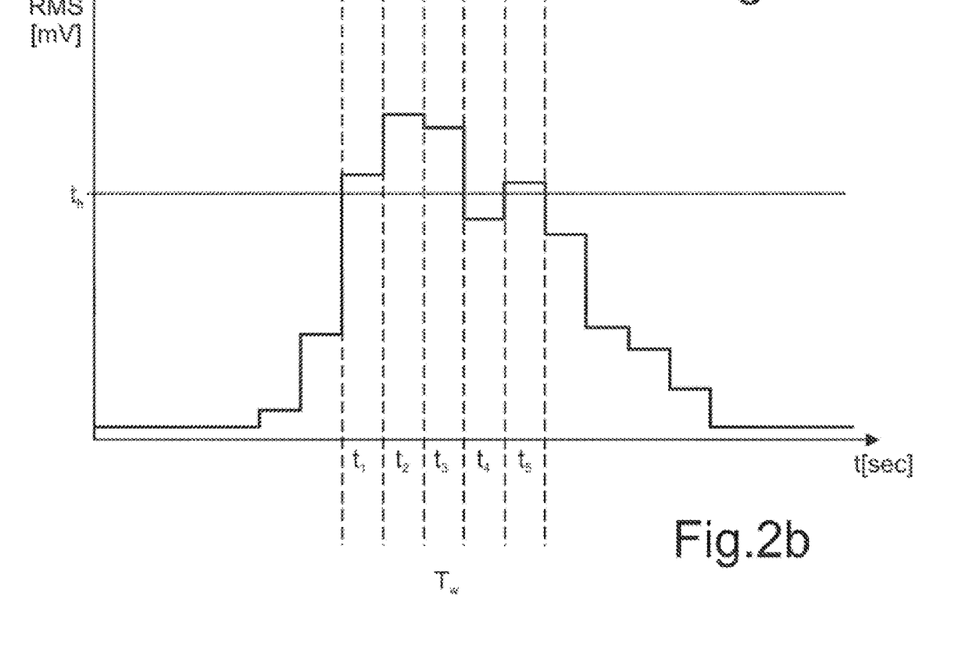

FIG. 2b shows how one embodiment of the method according to the invention evaluates the electromyographical signal in FIG. 2a.

Over a predetermined period of time ($t_n$), e.g. 1 second, the method calculates the RMS (Root Means Square) value for the electromyographical signal. This value is also referred to as the AMO (Average Muscle Output).

For each new calculation of the AMO, i.e. for each new period of time ($t_n$), the method compares the AMO against a threshold value ($T_h$). If the AMO is below the threshold value nothing further will occur and the method will calculate a new AMO once a new period of time ($t_n+1$) begins.

If the AMO is above the threshold value ($t_1$) in a first period of time, the method will compare the AMO of the next four subsequent periods of time ($t_2$, $t_3$, $t_4$, $t_5$), i.e. within a time window ($T_W$) of five seconds. If the AMO of at least four of the five consecutive periods of time is above the threshold value, the method will generate an alarm signal.

It should be understood that when implementing the method, many different types of techniques could be used. For example it will for programming reasons typical be easier to analyze the signal by looking back in time, i.e. storing the signal and then shifting backwards in register while evaluating the signal against the predetermined power content.

The threshold value might be determined based on many different factors. Of course, the most important one is what the apparatus should detect. If the apparatus is for detecting epileptic seizures, the threshold value is typically derived from the MVC (Maximum Voluntary Contraction), which is the maximum electromyographic value a person voluntarily may produce. In other words the MVC is defined as the greatest amount of effort that an individual may exert. Usually, the effort is concentrated on one muscle or one joint. It is generally measured by monitoring the force or torque output from "Muscles Alive" by John V. Basmajian, Carlo De Luca, and Carlo J. Deluca. The threshold value may thus be the MVC, or may also be a percentage of the MVC, e.g. 60%-90% in particular 80% of the MVC. The threshold may even be above MVC as muscle events from seizures can be larger than the MVC.

Figure 3A:
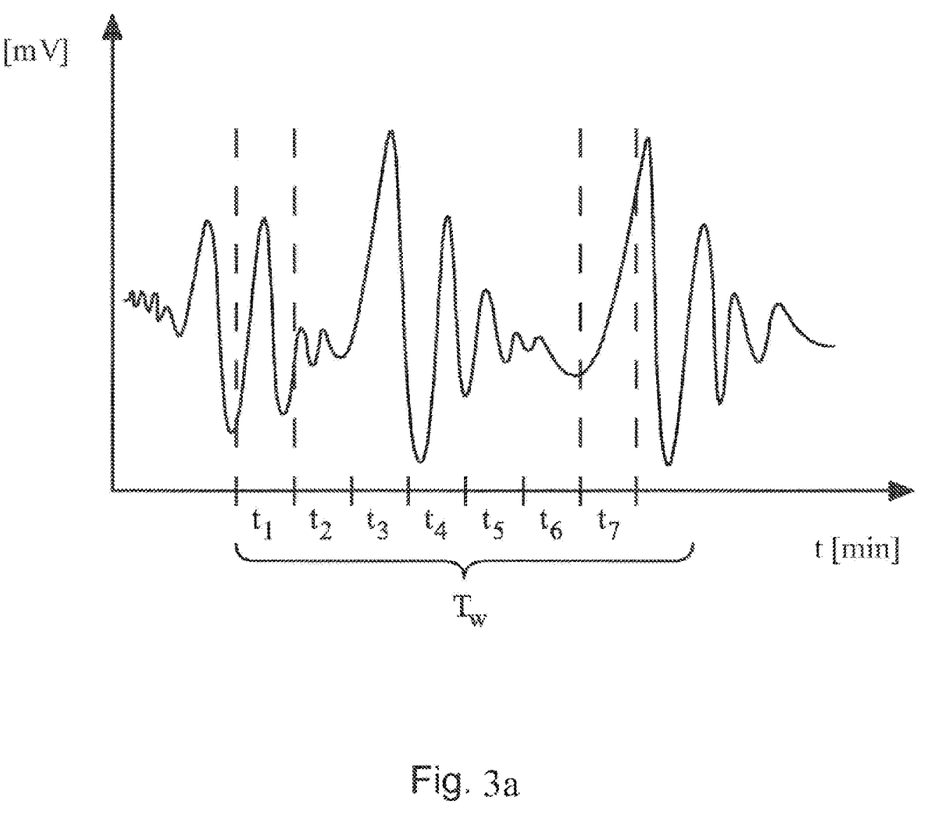
FIGS. 3a, 3b and 3c shows representatively an electromyographic signal and sections thereof transformed into the frequency domain.

FIG. 3a shows a representation of an electromyographic signal as detected from a sensor 2 attached to the skin surface of a person.

Figure 3B:
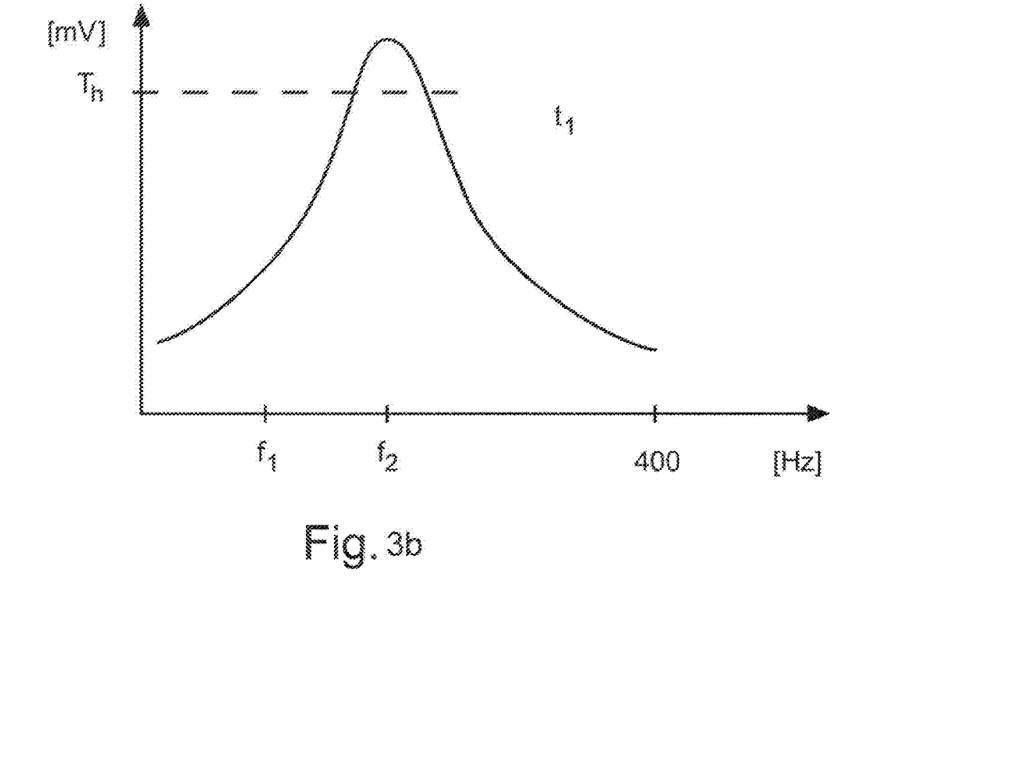

In one embodiment according to the invention the method for monitoring muscle activity will continuously transform the electromyographic signal into the frequency domain for each sub-time window $t_1$,-$t_7$. FIG. 3b shows the frequency transformed section of the electromyographical signal within the sub-time window $t_1$.

The frequency transformation is evaluated within 0-400 Hz as this is the frequency range wherein the muscles primarily work and thus contain most of the energy content.

It has been shown that the frequency profile of the electromyographic signal will change over time and during strenuous muscle activity. Thus, monitoring this change can be of interest in different situations.

Figure 3C:
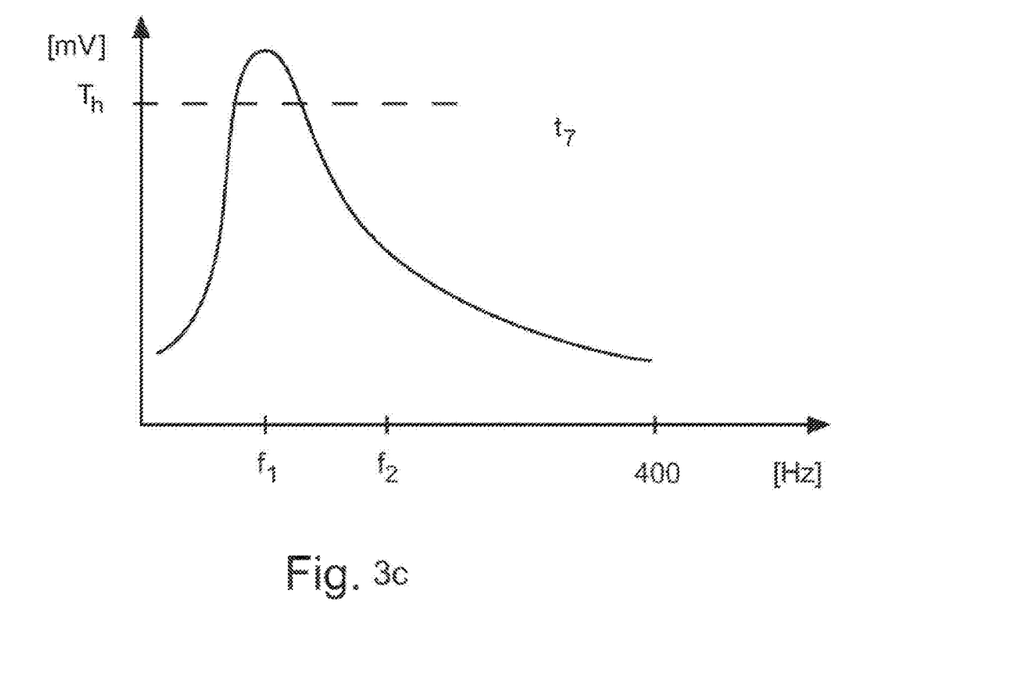

As can be seen in FIG. 3b the majority of the frequency content is gathered around $f_2$ and exceeds the threshold values $T_h$. This activates the time window $T_w$. If a part of the frequency transformed electromyographic signal within this time window continuously stays above the threshold window and changes to a lower frequency $f_1$ as occurs in sub-time window $t_7$ as shown in FIG. 3c it may be an indication that the muscles are getting fatigued indicating a possible epileptic seizure. This may consequently generated an event signal or an alarm.

Alternatively, if the method is used to monitor a person during an exercise session it can be used as an indication during heavy exercise that the muscles has been fully loaded.

It shall be understood that the above embodiments are examples and that many other embodiments may be provided within the scope of the invention. The method and apparatus described can thus be used to measure many types of muscle activity and not only in combination with epileptic seizures but also both voluntary and involuntary muscle activity within other areas, such as for example voluntary physical exercise and involuntary spasms.

Example 1

Surface EMG (Electromyographic) Measurement on a Person with Generalized Tonic Clonic Seizure In the following example Biceps Brachii were examined on a subject being 13 years old boy, weighing 35 kg and who is physically (unable to walk) and mentally disabled. The equipment used was an EMG recording equipment Nexus-4 recorder and usage of Ag/AgCl electrodes; Kendall H124SG Disposable electrodes with diameter 24 mm. The inter electrode distance was 34 mm.

The EMG signals were obtained from electrode pairs placed at Biceps Brachii and a reference electrode was placed on the bony surface of the subject's elbow. The electrode pairs were placed above each other in the longitudinal axes halfway the distal endplate zone, and in transversal direction the electrode pairs were placed at the surface away from the "Edge" of other muscles.

The EMG recorder (Nexus-4) was kept in an arm worn pocket applied to the person's arm opposite the arm with electrodes. Data was continuously transferred from the Nexus-4 via a Bluetooth connection to a lap top computer with Biotrace software in order to record the EMG data for approximately 10 hours. Afterwards data were analyzed in order to state whether it was possible to differentiate EMG signals during a Generalized Tonic Clonic Seizure from EMG signal during sleep and normal daily activity.

In the present case the threshold value, i.e. the predetermined power content, was set to 150 μV (micro Volt) mean value of 32 RMS values recorded within a second. This was determined after establishing the subjects MVC to be 190 μV (80% of 190 μV being approximately 150 μV).

Although the signal analyzed is different the method used was similar to that described in respect to FIGS. 2a and 2b above, thus, in order for easy understanding references has beep introduced corresponding to the references in FIGS. 2a and 2b.

The method used analyzed the signal over predetermined time windows ($T_w$) of five seconds. Each predetermined time window was divided up into five predetermined sub-time windows ($t_1$, $t_2$, $t_3$, $t_4$, $t_5$), each being one second. The AMO for each sub-time window was then calculated. If the AMO in at least four out of five sub-time windows was above the threshold value, i.e. 150 μV, an event signal was generated.

Figure 4:
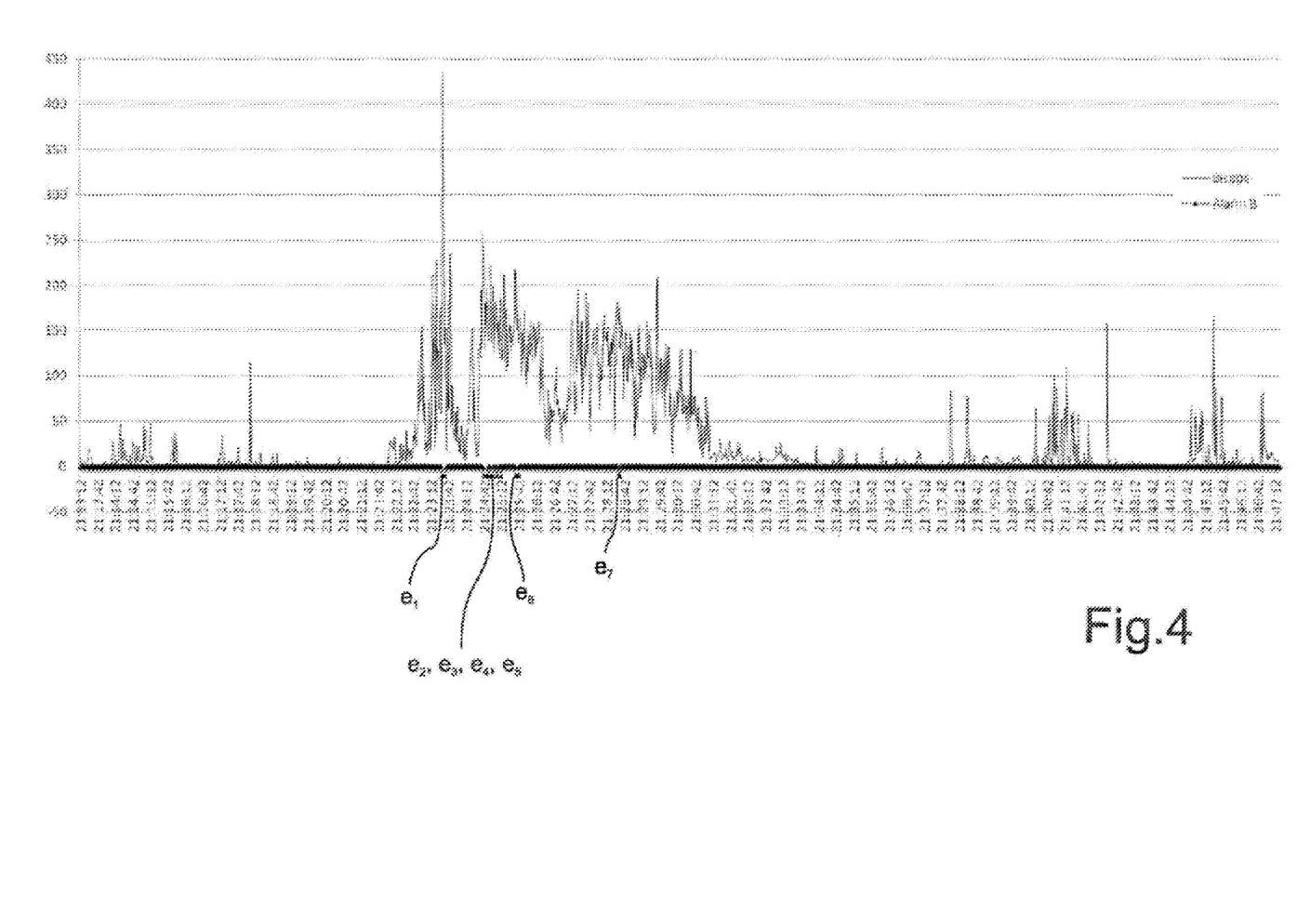
FIG. 4 shows a graph of a detected epileptic seizure and corresponding generated events.

The data recorded has been plotted in the graph shown in FIG. 4.

As may be seen several events $e_1$, $e_2$, $e_3$, $e_4$, $e_5$, $e_6$ and $e_7$ were generated based on event signals generated from above method in the period from 21:23:24 to 21:28:30 indicating that a seizure is occurring. The events have been illustrated as triangles in FIG. 4.

At all events it may be seen that the signal was detected as being above 150 μV for an extended period of time as described above. In particular at the event $e_7$ generated at 21:28:30 it can be observed that the signal (and thereby the power content) was fluctuating just around 150 μV. This generate only one event in contrary to the time 21:25:06 were several events $e_2$, $e_3$, $e_4$ and $e_5$ were generated as a majority of the power content was above the threshold valued.

In the period after the seizure (21.30-22.08) the patient is restless in his sleep which results in periods of activity. At 21.41-21.42 and again 22.05-22.06 the sits up in bed which results in signal peaks above 150 μV. However, these periods of activity only takes a short period of time and only with one peak above the threshold limit no event signal is generated. Thus, it was avoided that false events were generated.

When reading the above it should be born in mind that the subject is physically handicapped and that what seems like a simple action to us, e.g. moving around in bed or sitting up in bed requires considerable effort. Thus, such simple actions may generate sporadic peaks which are above 150 μV or even higher.

It should be understood that the MVC values are very dependent on the individual subject. For example in the current case where the MVC is approx. 190 μV work above 150 μV for the Biceps Brachii will be difficult to maintain for longer periods. However, for other subjects, for example athletes, the MVC may be significantly higher, for example 1200 μV or even more.

The results showed that by using the described setup and the method as disclosed herein it is possible to detect a Generalized Tonic Clonic Seizure while at the same time avoiding false alarms.

In order to reduce processing and thereby power, an activation circuit has been inserted in the device used in the current Example 1. The activation circuit continuously measures the, EMG signals and compares these to a preset activation value. The preset activation value is in the current setup set to 100 μV, which is approx. 50% the subject's MVC. In case the measured amplitude of the EMG signal is equal to or above the preset activation value, the activation circuit wakes up the processing unit. The processing unit subsequently processes the incoming data according to the appropriate algorithm, e.g. the above described method. In case of an event the radio unit is consequently powered up in order to transmit the event to the user.

Such an activation circuit requires considerably less power than continuously running the processing unit. Thus, by waking up the processing and radio unit only when the EMG signal is above the preset activation value, the power consumption of the apparatus is reduced significantly, which accordingly increases battery lifetime significantly.

Example 2

Surface EMG Measurement on a Person with Generalized Tonic Clonic Seizure

In the following example Biceps Brachii and Triceps Brachii were examined on a subject being 13 years old boy, weighing 35 kg and who is physically (unable to walk) and mentally disabled. The equipment used was an EMG recording equipment Nexus-4 recorder and usage of Ag/AgCl electrodes; Kendall H124SG Disposable electrodes with diameter 24 mm and inter electrode distance of 34 mm.

Basically it is the same subject and time period as in Example 1, thus the graph for the Biceps Brachii is the same. However, in this Example the detected signal of Triceps Brachii has been included.

The EMG signals were obtained from electrode pairs placed at Biceps Brachii and the antagonistic Triceps Brachii and the reference electrode was placed on the bony surface of the subject's elbow. The electrode pairs were placed above each other in the longitudinal axes halfway the distal endplate zone, and in transversal direction the electrode pairs were placed at the surface away from the "Edge" of other muscles. In the present case the EMG recorder (Nexus-4) was kept in an arm worn pocket applied to the person's arm opposite the arm with electrodes. Data was continuously transferred from the Nexus-4 via a Bluetooth connection to a lap top computer with Biotrace software in order to record the EMG data for approximately 10 hours.

When a person bend the upper arm voluntarily the Biceps Brachii will contract whereas the Triceps Brachii will be relaxed, when the arm is stretched the opposite holds true. In the present case we have EMG data from a patient with Generalized Tonic Clonic Seizure and observe whether the power output is significant from both biceps and triceps compared to EMG during sleep and normal daily activity. The data has been plotted in the graph shown in FIG. 5a for the Biceps Brachii (identical to FIG. 4 but over a longer time period) and FIG. 5b for the Triceps Brachii. Along the axis of abscissa (X-axis) time in second is plotted and along the axis of ordinate (Y-axis) the mean value of 32 RMS values within a second in μV (microVolt) is plotted.

As may be seen both Biceps and Triceps contracts during a seizure, which typically do not occur by voluntary movement where one will relax when the other contracts. With the given fact in mind it is possible to have an even more precise indication of when a seizure is ongoing with a combination of the event criteria of Biceps and Triceps and only create an event when both event criteria are full filled.

Figure 5A:
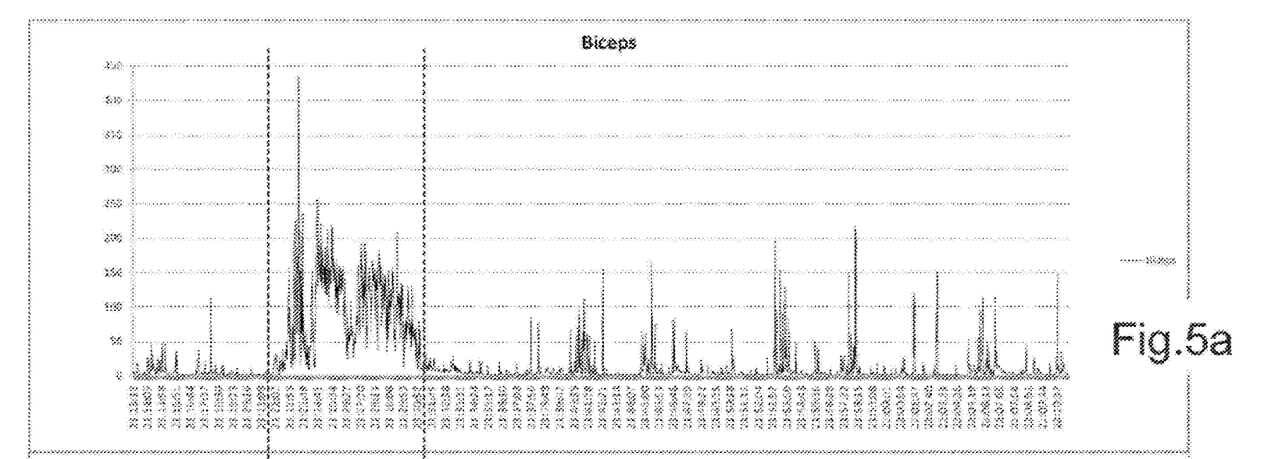
FIGS. 5a and 5b shows graphs of electromyographic signals for Biceps Brachii and Triceps Brachii respectively.
Figure 5B:
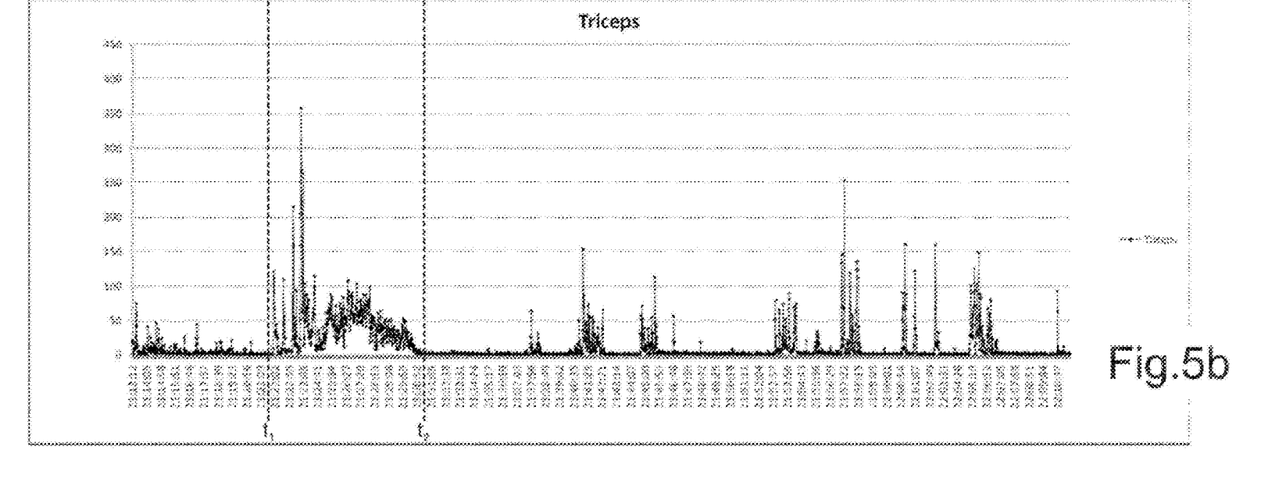

As it can be observed significant activity takes place between 21.22-21.30 ($t_1$,-$t_2$) where the Tonic Clonic seizure is ongoing. In the period after the seizure (21.30-22.08) the patient is restless in his sleep and in periods he moves actively around. At 21.41-21.42 and again 22.05-22.06 the patient sits up in the bed. The EMG signals are though significant lower than during Tonic Clonic Seizure.

Figure 5C:
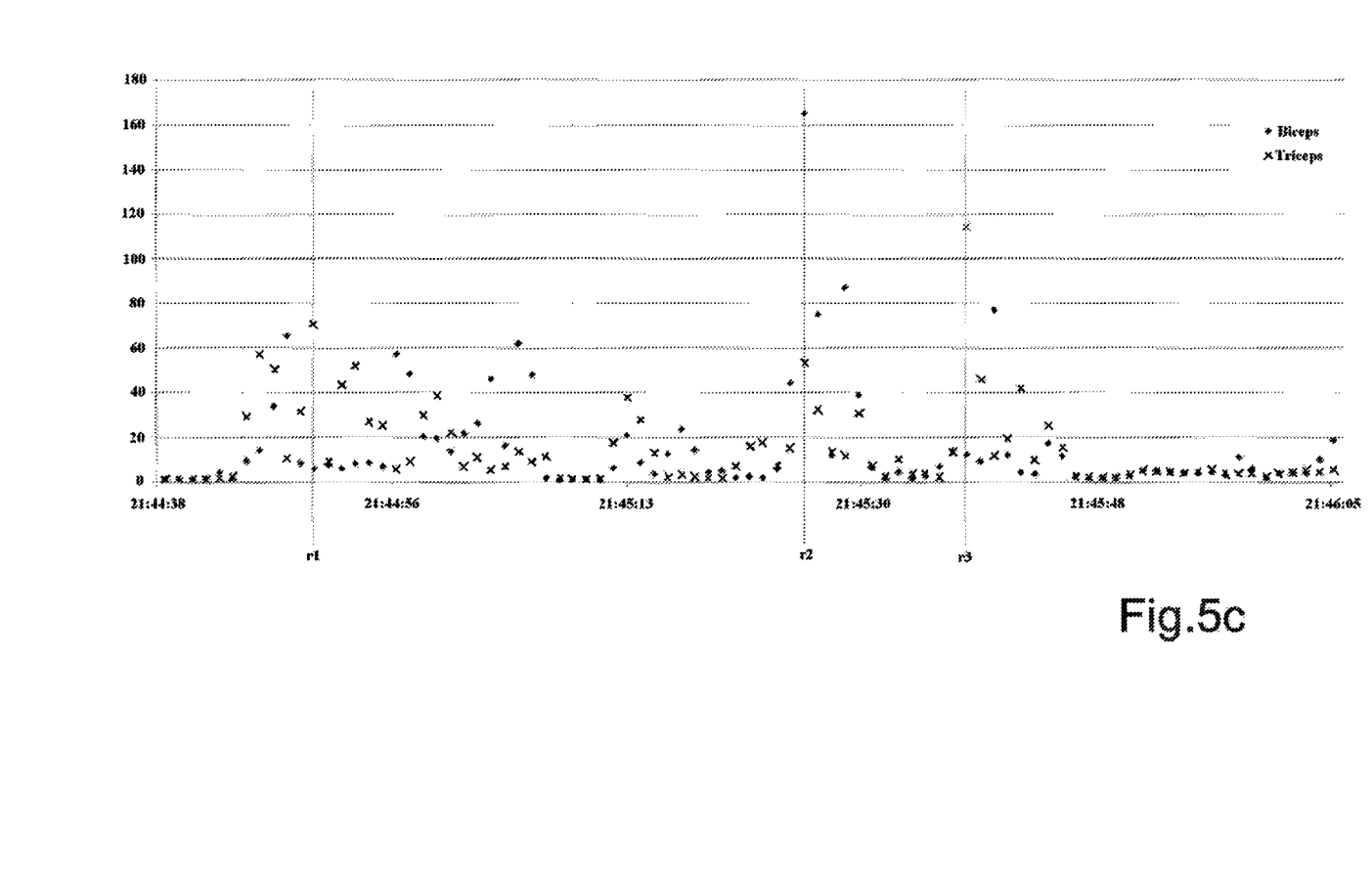

In FIG. 5c the time period shows an enlarged view of the graph plotted in FIGS. 5a and 5b. The illustrated time interval is between 21:44 and 21:46 where the subject is not having an epileptic seizure. In the enlarged section it can more easily be observed that when either the Biceps Brachii or the Triceps Brachii contracts (i.e. the value for the respective data set will increase) the other will relax (i.e. the value for the other data set will decrease).

To help illustrate reference lines $r_1$, $r_2$ and $r_3$ has been added to FIG. 5c. From here it can be seen more clearly that when the Triceps Brachii is contracted a relative high power content is generated compared to the Biceps Brachii which is relaxed thereby generating a relative lower power content as shown at $r_1$, and $r_3$. The opposite (i.e. the Biceps Brachii is contracted and the Triceps Brachii is relaxed) is shown at $r_2$.

However, the above is not completely consistent for all of FIG. 5c. This is because of some different factors, e.g. the resolution of the sampled signal, that each point is calculated as an RMS values over one second and that the contraction and relaxation of a muscle is a gradual movement. However, comparing it to the time period where epileptic seizure is occurring it is clear that during such a seizure considerable activity in both muscles are occurring simultaneously for a prolonged period of time.

The results showed that by using the detection of an antagonistic muscle pair during seizure it will be possible to more precisely specify onset of a Generalized Tonic Clonic Seizure while at the same time to a higher degree avoid false alarms.

Thus, a method may be provided wherein the power content from an at least first and second electromyographic signal detected from an antagonistic muscle pair respectively are compared, and an event signal is generated if the power content of the first and second electromyographic signal is above a first and second threshold value respectively.

It should be understood that generating event signals based on detection of two antagonistic muscles may be done independently from looking at the power content of an electromyographic signal.

The invention claimed is:

1. An apparatus for detecting electromyographic signals and monitoring muscle activity, said apparatus comprising:
   a sensor, for detecting the electromyographic signals,
   processing means, which, if the electromyographic signals exceed an activation value, then apply an integration algorithm or a frequency transformation algorithm to the detected electromyographic signals, and determine whether the integrated or frequency transformed signals are above a predetermined power content within a first predetermined time window and wherein an event signal is generated if the integrated or frequency transformed electromyographic signals are above the predetermined power content for at least a number of times within a second predetermined time window and wherein the event signal triggers an event, and,
   first communication means, for transmitting the detected electromyographic signals from the sensor to the processing means.

2. An apparatus according to claim 1, wherein the processing means are comprised within the sensor.

3. An apparatus according to claim 1, wherein the processing means are comprised within a peripheral device.

4. An apparatus according to claim 3, wherein the peripheral device is selected from the group of handheld devices consisting of a PDA, an iPOD®, a cell phone and a custom peripheral device.

5. An apparatus according to claim 3, wherein the peripheral device is a personal computer.

6. An apparatus according to claim 1, wherein the first communication means transmits the electromyographic signals via wireless transmission.

7. An apparatus according to claim 1, wherein the first communication means transmits the electromyographic signals via an electrical connection.

8. An apparatus according to claim 1, further comprising a second communication means for providing communication between the sensor and a peripheral device.

9. An apparatus according to claim 1 further comprising an alarm activated if the event is triggered.

10. An apparatus according to claim 1, wherein the apparatus has two or more sensors for detecting the electromyographic signals.

11. An apparatus according to claim 10, wherein an event signal is generated if the electromyographic signals are above a predetermined power content for at least one sensor.

12. An apparatus according to claim 1, further comprising an activation circuit which activates the processing means when the electromyographic signal is above the activation value.

13. An apparatus according to claim 1, wherein the activation value is between 20%-60%, in particular 50% of a maximum voluntary contraction.

14. A method for monitoring muscle activity based on an electromyographic signal, comprising the steps of:
   detecting the electromyographic signal,
   determining if the detected electromyographic signal is above an activation value, and if so, then
   applying an integrating algorithm or a frequency transformation algorithm to the detected electromyographic signal,
   evaluating and determining whether the integration or frequency transformed electromyographic signal is above a predetermined power content within a first predetermined time window,
   generating an event signal if the integration or frequency transformed electromyographic signal is determined to be above the predetermined power content for at least a predetermined number of times within a second predetermined time window, and
   triggering an event if an event signal is generated.

15. A method according to claim 14, wherein the method further comprises frequency filtering the electromyographic signal before evaluating the electromyographic signal.

16. A method according to claim 15, wherein the electromyographic signal is frequency filtered by a bandpass filter, lowpass filter or a highpass filter.

17. A method according to claim 14 further comprising applying an integration algorithm to the electromyographic signal and generating the event signal if the resulting integrated electromyographic signal is above a predetermined power content.

18. A method according to claim 17 further comprising generating an event signal if the integrated electromyographic signal has an integrated value above a predetermined threshold amplitude value for a predetermined number of times within the second predetermined time window.

19. A method according to claim 18, wherein the predetermined number of times is four and the second predetermined time window is five seconds.

20. A method according to claim 18, wherein the predetermined threshold amplitude value is greater than a maximum voluntary contraction value of the user.

21. A method according to claim 18, wherein the predetermined threshold amplitude value is 60%-90%, in particular 80% of a maximum voluntary contraction value.

22. A method according to claim 17, wherein the integration algorithm is a RMS evaluation of the electromyographic signal.

23. A method according to claim 14, wherein the event triggered is an alarm.

24. A method according to claim 14 further comprising applying a frequency transformation algorithm to the electromyographic signal and generating the event signal if the resulting frequency transformed electromyographic signal is above a predetermined power content.

25. A method according to claim 24, wherein the frequency evaluating algorithm is a Fourier transformation of the electromyographic signal.

26. A method according to claim 14, wherein the activation value is between 20%-60%, in particular 50% of a maximum voluntary contraction.

27. A method according to claim 14, wherein electromyographic output signals from antagonistic muscle pairs are compared and an event signal is generated if both contract.

28. A method according to claim 14 further comprising comparing the power content from an at least first and second electromyographic signal detected from antagonistic muscle pairs respectively and generating an event signal if the power content of the first and second electromyographic signal is above a first and second threshold value respectively.

29. The apparatus according to claim 1 wherein the sensor is a skin mounted sensor.

30. The apparatus of claim 1 wherein the apparatus has one or more sensors for placement on the skin surface of a muscle, a muscle group or different muscles.

31. The method of claim 14 further comprising placing a sensor for detecting the electromyographic signal on a skin surface.

32. The method of claim 14 further comprising placing one or more sensors for detecting the electromyographic signal on a skin surface of a muscle, a muscle group or different muscles.

* * * * *